United States Patent
Omstead et al.

(10) Patent No.: US 10,436,717 B2
(45) Date of Patent: Oct. 8, 2019

(54) COMPOSITIONAL OPTICAL EMISSION SPECTROSCOPY FOR DETECTION OF PARTICLE INDUCED ARCS IN A FABRICATION PROCESS

(71) Applicant: Tokyo Electron Limited, Tokyo (JP)

(72) Inventors: Thomas Omstead, Boise, ID (US); Ke-Hung Chen, Boise, ID (US); Deepak Vedhachalam, Boise, ID (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 15/816,674

(22) Filed: Nov. 17, 2017

(65) Prior Publication Data

US 2018/0143141 A1 May 24, 2018

Related U.S. Application Data

(60) Provisional application No. 62/424,153, filed on Nov. 18, 2016.

(51) Int. Cl.
*G01N 21/73* (2006.01)
*G01J 3/443* (2006.01)

(52) U.S. Cl.
CPC .............. *G01N 21/73* (2013.01); *G01J 3/443* (2013.01)

(58) Field of Classification Search
CPC . G01N 21/31; G01N 21/73; G01J 3/30; G01J 3/42; G01J 3/443; H01J 37/32; H01J 37/32944; H01J 37/32082; H01L 21/66; H01L 21/3065; H01L 22/14; H01L 21/302; H01L 21/306; G06F 15/20; G01L 21/30

See application file for complete search history.

(56) References Cited

U.S. PATENT DOCUMENTS

| | | | |
|---|---|---|---|
| 3,059,611 A | 10/1962 | Fury | |
| 3,612,692 A | 10/1971 | Kruppa et al. | |
| 4,147,435 A | 4/1979 | Habegger | |
| 5,014,217 A * | 5/1991 | Savage | C23C 16/52 |
| | | | 204/192.33 |
| 5,308,414 A | 5/1994 | O'Neill et al. | |
| 5,347,460 A | 9/1994 | Gifford et al. | |
| 5,353,790 A | 10/1994 | Jacques et al. | |
| 5,450,205 A | 9/1995 | Sawin et al. | |
| 5,648,198 A | 7/1997 | Shibata | |

(Continued)

FOREIGN PATENT DOCUMENTS

| | | |
|---|---|---|
| CN | 101038860 A | 9/2007 |
| CN | 101221891 A | 7/2008 |

(Continued)

OTHER PUBLICATIONS

De Schepper, P. et al., "Pattern Roughness Mitigation of 22 nm Lines and Spaces: The Impact of a H2 Plasma Treatment", Plasma Processes and Polymers, Sep. 2014, 10 pp. [retrieved on Jun. 7, 2016] <DOI: 10.1002/ppap.201400078>.

(Continued)

*Primary Examiner* — Jamil Ahmed
(74) *Attorney, Agent, or Firm* — Oblon, McClelland, Maier & Neustadt, L.L.P.

(57) ABSTRACT

Described herein are architectures, platforms and methods for detecting and analyzing anomalous events (i.e., arcing events) from spectral data gathered during a wafer fabrication process.

20 Claims, 7 Drawing Sheets

(56) References Cited

U.S. PATENT DOCUMENTS

| | | |
|---|---|---|
| 5,751,416 A | 5/1998 | Singh et al. |
| 5,885,472 A | 3/1999 | Miyazaki et al. |
| 5,980,767 A | 11/1999 | Koshimizu et al. |
| 6,060,328 A | 5/2000 | En et al. |
| 6,081,334 A | 6/2000 | Grimbergen et al. |
| 6,090,302 A | 7/2000 | Smith, Jr. et al. |
| 6,132,577 A | 10/2000 | Smith, Jr. et al. |
| 6,374,832 B2 | 4/2002 | Chow et al. |
| 6,381,008 B1 | 4/2002 | Branagh et al. |
| 6,535,779 B1 | 3/2003 | Birang et al. |
| 6,564,114 B1 | 5/2003 | Toprac et al. |
| 6,582,618 B1 | 6/2003 | Toprac et al. |
| 6,703,250 B2 | 3/2004 | Chiu |
| 6,745,095 B1 | 6/2004 | Ben-Dov et al. |
| 6,815,653 B2 | 11/2004 | Tsay et al. |
| 6,825,920 B2 | 11/2004 | Lam et al. |
| 6,830,939 B2 | 12/2004 | Harvey et al. |
| 6,911,157 B2 | 6/2005 | Edamura et al. |
| 6,958,484 B2 | 10/2005 | Mitrovic |
| 7,241,397 B2 | 7/2007 | Fink et al. |
| 7,312,865 B2 | 12/2007 | Chen |
| 7,328,126 B2 | 2/2008 | Chamness |
| 7,334,477 B1 | 2/2008 | Pirkle |
| 7,591,923 B2 | 9/2009 | Mitrovic et al. |
| 7,906,032 B2 | 3/2011 | Yamashita |
| 7,959,970 B2 | 6/2011 | Gaudet et al. |
| 8,048,326 B2 | 11/2011 | Yue et al. |
| 8,154,721 B2 | 4/2012 | Chen et al. |
| 8,158,017 B2 | 4/2012 | Hudson |
| 8,173,451 B1 | 5/2012 | Tian et al. |
| 8,415,884 B2 | 4/2013 | Chen et al. |
| 8,416,509 B2 | 4/2013 | Yi et al. |
| 8,513,583 B2 | 8/2013 | Corke et al. |
| 8,553,218 B2 | 10/2013 | Tinnemans et al. |
| 8,877,080 B2 | 11/2014 | Chen et al. |
| 8,883,024 B2 | 11/2014 | Chen et al. |
| 9,200,950 B2 | 12/2015 | Lian et al. |
| 9,209,950 B2 | 12/2015 | Lian et al. |
| 9,760,008 B2 | 9/2017 | Devilliers |
| 9,842,726 B2 | 12/2017 | Daniels et al. |
| 2001/0046769 A1 | 11/2001 | Chow et al. |
| 2002/0029851 A1 | 3/2002 | Edamura et al. |
| 2003/0132195 A1 | 7/2003 | Edamura et al. |
| 2004/0008336 A1 | 1/2004 | Lam et al. |
| 2004/0058359 A1 | 3/2004 | Mei et al. |
| 2004/0104681 A1 | 6/2004 | Mitrovic |
| 2004/0235303 A1 | 11/2004 | Wong et al. |
| 2005/0241669 A1 | 11/2005 | Wodecki |
| 2006/0006139 A1 | 1/2006 | Johnson et al. |
| 2007/0128876 A1 | 6/2007 | Fukiage |
| 2007/0238199 A1 | 10/2007 | Yamashita |
| 2008/0186473 A1 | 8/2008 | Lee |
| 2009/0065025 A1 | 3/2009 | Urbanowicz et al. |
| 2009/0280581 A1 | 11/2009 | Hudson |
| 2009/0325387 A1 | 12/2009 | Chen et al. |
| 2010/0081285 A1 | 4/2010 | Chen et al. |
| 2011/0139748 A1 | 6/2011 | Donnelly et al. |
| 2011/0174776 A1 | 7/2011 | Kabe et al. |
| 2012/0006351 A1 | 1/2012 | Jun et al. |
| 2012/0085494 A1 | 4/2012 | Uchida et al. |
| 2012/0091097 A1 | 4/2012 | Chen et al. |
| 2012/0175060 A1 | 7/2012 | Hudson et al. |
| 2013/0016344 A1 | 1/2013 | Bullock et al. |
| 2013/0141720 A1 | 6/2013 | Park et al. |
| 2015/0241272 A1 | 8/2015 | Lian et al. |
| 2016/0268108 A1* | 9/2016 | Daniels ............. H01J 37/32091 |

FOREIGN PATENT DOCUMENTS

| | | | |
|---|---|---|---|
| CN | 102282654 A | | 12/2011 |
| CN | 102788916 A | * | 11/2012 ............. G01N 21/73 |
| CN | 103117202 B | | 9/2015 |
| EP | 0 652 415 A1 | | 10/1994 |
| JP | 2016-541119 A | | 12/2016 |
| KR | 10-2012-0126418 A | | 11/2012 |
| TW | 589659 | | 6/2004 |
| WO | 02/091453 A1 | | 11/2002 |
| WO | 2005-527984 A | | 9/2005 |
| WO | 2005/111265 A1 | | 11/2005 |
| WO | WO 2015/130433 A1 | | 9/2015 |

OTHER PUBLICATIONS

International Preliminary Report on Patentability dated Oct. 11, 2018 in International Application No. PCT/US2017/024138, filed Mar. 24, 2017 15 pp.

International Search Report & Written Opinion dated Aug. 18, 2017 in International Application No. PCT/US2017/024138, filed Mar. 24, 2017 18 pp.

International Search Report & Written Opinion dated Jun. 29, 2018 in International Application No. PCT/US2018/022253, filed Mar. 13, 2018 13 pp.

Notification of Examination Opinions dated May 11, 2018 in Taiwanese Patent Application No. 106110455 (w/ English language translation) 12 pp.

Yamaguchi, T. et al., "Direct current superposed dual-frequency capacitively coupled plasmas in selective etching of SiOCH over SiC", Journal of Physics D Applied Physics, Dec. 2011, 25 pp. [retrieved on May 6, 2016] <DOI: 10.1088/0022-3727/45/2/025203>.

Office Action dated Sep. 19, 2018 in U.S. Appl. No. 15/453,555.

Combined Chinese Office Action and Search Report dated Mar. 3, 2016 in Chinese Patent Application No. 201380054482.2 (with English translation), 12 pages.

Ventzek, P.L.G., et al., "Formation, Nature, and Stability of the Arsenic-Silicon-Oxygen Alloy for Plasma Doping of Non-Planar Silicon Structures", Applied Physics letters, vol. 105, 2014, pp. 262102-1-262102-5 with cover page.

Combined Taiwanese Office Action and Search Report dated May 25, 2015 in Taiwanese Patent Application No. 102137525 (with English translation), 19 pages.

White, D.A., "Multivariate Analysis of Spectral Measurements for the Characterization of Semiconductor Processes", Dissertation presented Apr. 2002, at Massachusetts Institute of Technology, pp. 1-357.

Goodlin, B.E., "Multivariate Endpoint Detection of Plasma Etching Processes", Dissertation presented Apr. 2002, at Massachusetts Institute of Technology, pp. 1-226.

International Search Report and Written Opinion dated Mar. 19, 2014 in PCT/US2013/065378, 22 pages.

Yue, H.H., et al., "Plasma Etching Endpoint Detection Using Multiple Wavelengths for Small Open-Area Wafers", J. Vac. Sci. Technol. A, vol. 19 No. 1, 2001, pp. 66-75 with cover page.

White, D., et al., "Low-Open Area Endpoint Detection using a PCA based $T^2$ Statistic and Q Statistic on Optical Emission Spectroscopy Measurements", IEEE Transactions on Semiconductor Manufacturing, vol. 13 No. 2, May 2000, pp. 1-30.

Goodlin, B. E., et al., "Quantitative Analysis and Comparison of Endpoint Detection Based on Multiple Wavelength Analysis", 201st Meeting of the Electrochemical Society, International Symposium on Plasma Processing XIV, Abs. 415, May 2002, pp. 1-30.

Chinese Office Action dated Oct. 31, 2016 in Chinese Patent Application No. 201380054482.2 (with English translation), 10 pages.

Japanese Office Action dated Jul. 5, 2016 in Japanese Patent Application No. 2015-537813 (with English translation), 4 pages.

Combined Taiwanese Office Action and Search Report dated Jan. 2, 2018 in Taiwanese Patent Application No. 105137371 (with English translation), 16 pages.

International Search Report and Witten Opinion dated Jan. 31, 2017 in PCT/US2016/062017, 13 pages.

Master's Thesis of Jae-Wook Lee, presented at University of California, Berkeley, Jul. 1, 2000, 69 pages.

Shannon, S., et al., "A Spatially Resolved Optical Emission Sensor Plasma Etch Monitoring", Appl. Phys. Lett., vol. 71 No. 11, Sep. 1997, pp. 1467-1468.

(56) References Cited

OTHER PUBLICATIONS

Selwyn, G.S., "Optical Diagnostic Techniques for Plasma Processing", AVS Press, 1993, Relevant chapter 3 on Optical Emission Spectroscopy (OES) is provided, pp. 26-80 with title and bibliographic information pages.
International Search Report and Written Opinion dated Jan. 29, 2015 in PCT/US2014/63565, 8 pages.
International Search Report and Written Opinion dated Mar. 12, 2018 in PCT/US2017/062316, 13 pages.

* cited by examiner

Optical Emission - Sorted by Wavelength

| | | | | | | | | | | | | | | |
|---|---|---|---|---|---|---|---|---|---|---|---|---|---|---|
| Zn | 213.9 | CO | 288.2 | Si | 324.8 | Cu | 365.3 | Ti | 403.3 | Ga | 451.0 | In | 546.1 | Hg | 646.9 | F | 739.9 |
| SiO | 230.0 | AlCl | 288.4 | CO2 | 326.8 | N2 | 365.5 | Hg | 404.7 | Hg | 451.1 | Ar | 549.6 | N2 | 654.5 | Cl | 741.4 |
| Ni | 232.0 | CF2 | 289.8 | CO2 | 327.4 | Au | 366.3 | Hg | 405.1 | SiN | 451.1 | CO | 559.3 | N2 | 656.3 | F | 742.6 |
| SiO | 234.4 | AlCl | 292.1 | CF | 327.4 | Cu | 367.2 | N2 | 405.9 | CCl | 460.0 | CCl | 561.0 | H | 662.0 | Ar | 750.4 |
| NO | 237.0 | Ge | 293.0 | Pt | 328.2 | Zn | 369.9 | Co | 407.4 | Zn | 468.0 | Zn | 563.3 | CO | 662.4 | N2 | 750.4 |
| SiO | 238.8 | Ta | 294.4 | Ga | 330.3 | Zn | 370.5 | He | 408.7 | Zr | 468.8 | Zr | 575.5 | N2 | 667.8 | He | 751.5 |
| SiO | 239.3 | BCl | 294.5 | He | 330.9 | N2 | 371.1 | N2 | 409.5 | N2 | 469.5 | S | 577.0 | Hg | 670.5 | Cl | 754.7 |
| CF | 240.4 | Pt | 295.3 | N2 | 331.2 | Co | 372.0 | Fe | 410.0 | In | 470.5 | Br | 578.0 | WF | 677.4 | F | 755.2 |
| SiO | 241.4 | Au | 296.2 | N2 | 334.5 | Zn | 373.5 | Fe | 411.6 | SiN | 471.0 | Zr | 579.1 | Hg | 678.9 | N2 | 757.3 |
| Fe | 242.8 | NO | 297.7 | N2 | 334.9 | Ti | 375.5 | N2 | 412.7 | SiN | 471.3 | SiN | 580.4 | N2 | 683.4 | F | 760.7 |
| CF2 | 245.8 | AlCl | 301.2 | Ni | 336.0 | NH | 379.8 | Mo | 414.2 | N2 | 472.2 | Zn | 585.0 | CN | 685.6 | N2 | 762.6 |
| CF | 247.5 | Pt | 303.9 | Ge | 337.1 | N2 | 380.5 | N2 | 414.4 | Zr | 474.0 | Zr | 585.4 | N2 | 687.0 | Cl | 771.8 |
| C | 247.9 | Ge | 306.4 | OH | 341.5 | Ni | 382.0 | He | 415.9 | Zr | 477.2 | Zr | 587.6 | He | 687.5 | Cl | 774.5 |
| NO | 247.9 | CF2 | 306.5 | Pt | 344.8 | He | 385.8 | N2 | 417.2 | Br | 478.7 | Br | 590.6 | N2 | 690.2 | N2 | 775.3 |
| Fe | 248.3 | Co | 307.0 | CCl | 346.2 | Ni | 386.2 | Ga | 418.1 | Zn | 481.1 | Zn | 595.9 | N2 | 691.0 | F | 775.5 |
| SiO | 248.7 | Ta | 308.2 | Al | 349.2 | Co | 386.4 | CN | 419.7 | Mo | 481.6 | Zr | 601.4 | N2 | 692.6 | CN | 777.2 |
| CF2 | 248.8 | BCl | 308.9 | Cl2 | 350.1 | N2 | 386.8 | Mo | 420.1 | N2 | 481.7 | Ar | 603.2 | Ar | 696.5 | O | 777.9 |
| CO | 249.2 | NO | 308.9 | OH | 352.0 | Zr | 387.1 | CN | 420.4 | SiN | 483.5 | C | 604.6 | F | 696.6 | SiF | 780.0 |
| CF2 | 249.8 | Au | 309.3 | Al | 353.3 | N2 | 388.3 | CN | 421.6 | CN | 484.8 | N2 | 607.0 | N2 | 703.7 | F | 787.3 |
| B | 249.8 | CF2 | 310.4 | N2 | 354.8 | Zr | 388.9 | He | 425.4 | Cr | 486.1 | Ar | 608.0 | CO | 703.8 | CN | 789.6 |
| Si | 251.6 | Ge | 311.7 | N2 | 357.7 | Cr | 389.5 | N2 | 427.0 | N2 | 492.2 | CO | 612.7 | O | 706.8 | N2 | |
| CF2 | 251.9 | CCl | 312.3 | Au | 357.9 | SiF2 | 429.5 | W | 497.0 | H | 615.8 | N2 | 706.8 | | | | |
| Si | 252.4 | BCl | 312.6 | Hg | 358.6 | Mo | 390.2 | CH | 431.4 | He | 618.5 | O | 712.8 | | | | |
| Hg | 253.7 | CF2 | 313.2 | Hg | 359.0 | CN | 390.3 | Mo | 431.4 | O | 624.0 | He | 716.5 | | | | |
| CF2 | 255.1 | SiCl | 313.3 | Mo | 359.3 | N2 | 394.3 | H | 434.0 | F | 632.3 | N2 | 720.2 | | | | |
| CF | 255.8 | N2 | 313.4 | CO | 360.1 | Al | 394.4 | N2 | 434.4 | N2 | 634.9 | Zn | 725.4 | | | | |
| NO | 255.9 | CF2 | 313.6 | N2 | 360.5 | Al | 396.2 | Al | 435.8 | C2 | 636.2 | Zn | 725.7 | | | | |
| Cl2 | 256.0 | N2 | 315.9 | N2 | 361.4 | Cr | 396.5 | He | 436.8 | CO | 639.5 | N2 | 727.3 | | | | |
| Cl | 256.1 | SiCl | 318.8 | He | 363.4 | He | 399.8 | He | 438.8 | Cr | 641.4 | F | 728.1 | | | | |
| CCl | 258.0 | CO | 320.9 | Mo | 364.2 | N2 | 400.9 | SiF2 | 440.7 | O | 645.6 | O | 733.2 | | | | |
| CF2 | 259.5 | NO | 320.9 | CF2 | 365.0 | Hg | 402.6 | W | 443.8 | O | 646.7 | CN | 738.7 | | | | |
| NO | 259.6 | SiCl | 321.4 | | | | | He | 447.2 | | | | | | | |

FIG. 3 the spectral data from a plasma chamber during the wafer fabrication process. After a detection of occurrence of the anomalous event, an after-the-fact analysis of the gathered spectral data may be implemented to determine chemical specie(s) that may have caused the anomalous events or the arcing events.

COMPOSITIONAL OPTICAL EMISSION SPECTROSCOPY FOR DETECTION OF PARTICLE INDUCED ARCS IN A FABRICATION PROCESS

RELATED APPLICATIONS

This application is based on and claims priority to U.S. Provisional Patent Application No. 62/424,153 entitled "COMPOSITIONAL OPTICAL EMISSION SPECTROSCOPY FOR THE CHARACTERIZATION OF AN ETCH PROCESS" (Ref. No. TEA-138US1-PRO), filed on Nov. 18, 2016.

BACKGROUND

Plasma fabrication processes including etch processes may be subject to many problems affecting wafer yield, productivity, reliability, and cost. Such problems include arcing in a plasma chamber, where the arcing may be particle induced. It can be very difficult to diagnose such problems. In particular, diagnosis of such problems may involve opening the plasma or process chamber to the atmosphere. Once a chamber is opened to the atmosphere, the chamber is pumped down, purged, seasoned with as many wafers, and the etch process is requalified on production wafers. This cycle can be very costly in terms of tool utilization and fabrication productivity.

BRIEF DESCRIPTION OF THE DRAWINGS

The detailed description is described with reference to accompanying figures. In the figures, the left-most digit(s) of a reference number identifies the figure in which the reference number first appears. The same numbers are used throughout the drawings to reference like features and components.

FIG. 3 is an example illustration of pre-identified chemical—imprint identifications chart for different chemical species used in a wafer fabrication process as described herein.

DETAILED DESCRIPTION

Figure 1:
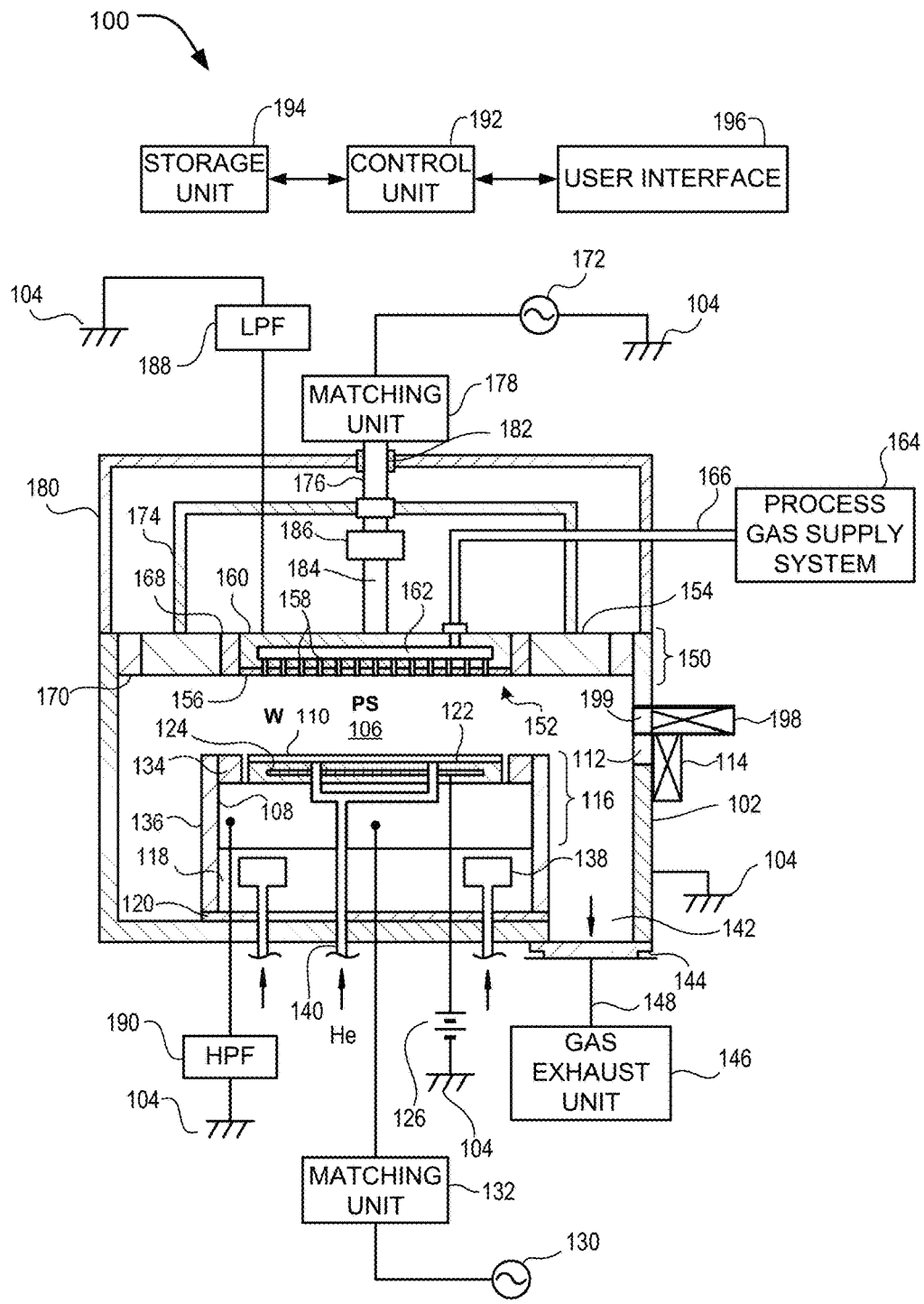
FIG. 1 is a cross-sectional view showing an example schematic configuration of a capacitively coupled plasma (CCP) processing system as described in accordance with embodiments herein.

Described herein are architectures, platforms and methods for detecting and analyzing anomalous events (i.e., arcing events) from a spectral data gathered during a wafer fabrication process. For example, a spectrometer is utilized to gather the spectral data from a plasma chamber during the wafer fabrication process. After a detection of occurrence of the anomalous event, an after-the-fact analysis of the gathered spectral data may be implemented to determine chemical specie(s) that may have caused the anomalous events or the arcing events.

In an embodiment, the determination of the chemical specie(s) may be implemented by initially establishing a distinct spectral characteristic (i.e., chemical—imprint identification) for each chemical specie utilized on each process step in the wafer fabrication process. For example, silicon or silicon-containing materials may be performed using a halogen-containing chemistry. Detectible optical emission spectroscopy (OES) species may include halides of silicon, and the halogen species itself (e.g. Cl, F, Br). Furthermore, for example etching of silicon oxide may be performed using a fluorine-containing chemistry, such as a fluorocarbon or hydrofluorocarbon gas. Detectable species may include halides of silicon, and the halogen species (F) that is released by the decomposition of the fluorocarbon or hydrofluorocarbon gas. Other detectable byproducts may include carbon monoxide (CO), and carbon dioxide (CO2), formed by reaction of oxygen (O) from a film or gas mixture with carbon (C) from the fluorocarbon or hydrofluorocarbon gas.

For the after-the-fact analysis of the spectral data, a manual determination of a particular time instant (of occurrence) of the anomalous event may be implemented. For example, a visual observation of the occurrence of the arcing event during the wafer production process may facilitate a manual observance of the particular time instant (i.e., reference point) in a data acquisition cycle, and a particular process step that is currently being performed when the arcing event occurred. In this example, the analysis of the spectral data and particularly, the analysis of the anomalous events, may be based upon spectra acquired within the particular time instant and/or the corresponding process step on that particular time instant. That is, for chemical specie(s) with substantially high intensities (i.e., above threshold) during that particular time instant, the stored spectral characteristics (i.e., chemical—imprint identifications) as mentioned above may be used to identify the culprit chemical specie(s).

In another embodiment, regarding the after-the-fact analysis of the spectral data, a photodiode installed in the plasma chamber may be utilized to detect the occurrence of the arcing events and this detection may trigger analysis of the anomalous events from the spectral data. For example, the photodiode detects the arcing events such as a substantial spike in light intensity at a particular time "t" during a particular process step in the wafer fabrication process. Similar to the discussion above regarding the manual observance of the particular time instant, the after-the-fact analysis of the spectral data may be focused upon the spectra acquired during the particular time "t" and/or the corresponding process step on the particular time "t," which may include a few micro seconds before and/or after the particular time "t" of the data acquisition cycle.

As described herein, the spectral data may include spectrally—resolved light emission signals from the plasma chamber. By spectrally—resolved light emission signals may indicate the light emission signals that were previously pre-identified, stored, and used for reference in the analysis of the anomalous events to identify the chemical species that caused the arcing events. Similarly, the spectral data may include non-spectrally—resolved light emission signals which may include generated particles that further enhance or increase the arcing events. In this case, the spectrometer may be utilized to determine the spectral characteristics of the non-spectrally—resolved light emission signals based on their distinct light intensities over a range of wavelength.

FIG. 1 shows a schematic cross-sectional view of an example of a capacitively coupled plasma (CCP) processing apparatus or plasma processing system 100 in accordance with embodiments herein. It is to be understood that other processing systems can be implemented, such as radial line slot antenna (RLSA) and inductively coupled plasma (ICP) processing systems may be implemented. In particular implementations, the plasma processing system 100 is used for wafer fabrication process, which may implement analysis of spectral data that includes spectrally—resolved light emission signals. By spectrally—resolved light emission signals means light emission signals or chemical species (e.g., Carbon (C), Carbon Dioxide (CO2), Silicon (Si), etc.) that were pre-identified through their distinct chemical imprint—identifications. At least one of these chemical species may cause an anomalous event (i.e., arcing event) during the wafer fabrication process and as such, the analysis of the anomalous event may help identify the chemical specie to be controlled and/or a process step to be modified for example.

The plasma processing system 100 may be used for multiple operations including ashing, etching, deposition, cleaning, plasma polymerization, plasma-enhanced chemical vapor deposition (PECVD), plasma-enhanced atomic layer deposition (PEALD) and so forth. Plasma processing can be executed within plasma processing chamber 102, which can be a vacuum chamber made of a metal such as aluminum or stainless steel. The plasma processing chamber 102 is grounded such to ground(s) 104. The plasma processing chamber 102 defines a processing vessel providing a process space PS 106 for plasma generation. An inner wall of the plasma processing chamber 102 can be coated with alumina, yttria, or other protectant. The plasma processing chamber 102 can be cylindrical in shape or have other geometric configurations.

At a lower, central area within the plasma processing chamber 102, a substrate holder or susceptor 108 (which can be disc-shaped) can serve as a mounting table on which, for example, a substrate W 110 to be processed (such as a semiconductor wafer) can be mounted. Substrate W 110 can be moved into the plasma processing chamber 102 through loading/unloading port 112 and gate valve 114. Susceptor 108 forms part of a lower electrode 116 (lower electrode assembly) as an example of a second electrode acting as a mounting table for mounting substrate W 110 thereon. Specifically, the susceptor 108 is supported on a susceptor support 118, which is provided at substantially a center of the bottom of plasma processing chamber 102 via an insulating plate 120. The susceptor support 118 can be cylindrical. The susceptor 108 can be formed of, e.g., an aluminum alloy. Susceptor 108 is provided thereon with an electrostatic chuck 122 (as part of the lower electrode assembly 116) for holding the substrate W 110. The electrostatic chuck 122 is provided with an electrode 124. Electrode 124 is electrically connected to DC power source 126 (direct current power source). The electrostatic chuck 122 attracts the substrate W 110 thereto via an electrostatic force generated when DC voltage from the DC power source 126 is applied to the electrode 124.

The susceptor 108 can be electrically connected with a high-frequency power source 130 via a matching unit 132. This high-frequency power source 130 (a second power source) can output a high-frequency voltage in a range from, for example, 2 MHz to 20 MHz. Applying high frequency bias power causes ions, in the plasma, generated in the plasma processing chamber 102, to be attracted to substrate W 110. A focus ring 134 is provided on an upper surface of the susceptor 108 to surround the electrostatic chuck 122. In addition, RF or microwave power (not shown) may be provided to the plasma processing chamber 102. RF or microwave power supplied to the plasma processing chamber; RF or microwave power pulse frequency; RF or microwave pulse duty cycle; and RF power supplied to a substrate holder or susceptor 108, in the plasma processing chamber 102 can be parameters that may be optimized to control the anomalous events when an after-the-fact analysis of the spectral data is implemented. By after-the-fact analysis means, the spectral data and particularly, the anomalous event is analyzed over a particular time instant of occurrence as further discussed below.

An inner wall member 136, which can be cylindrical and formed of, e.g., quartz, is attached to the outer peripheral side of the electrostatic chuck 122 and the susceptor support 118. The susceptor support 118 includes a coolant flow path 138. The coolant flow path 138 communicates with a chiller unit (not shown), installed outside the plasma processing chamber 102. Coolant flow path 138 is supplied with coolant (cooling liquid or cooling water) circulating through corresponding lines. Accordingly, a temperature of the substrate W 110 mounted on/above the susceptor 108 can be accurately controlled. A gas supply line 140, which passes through the susceptor 108 and the susceptor support 118, is configured to supply heat transfer gas to an upper surface of the electrostatic chuck 122. A heat transfer gas (also known as backside gas) such as helium (He) can be supplied between the substrate W 110 and the electrostatic chuck 122 via the gas supply line 140 to assist in heating substrate W 110.

An exhaust path 142 can be formed along an outer periphery of inner wall member 136 and an inner sidewall surface of the plasma processing chamber 102. An exhaust port 144 (or multiple exhaust ports) is provided in a bottom portion of the exhaust path 142. A gas exhaust unit 146 is connected to each exhaust port via gas exhaust line 148. The gas exhaust unit 146 can include a vacuum pump such as a turbo molecular pump configured to decompress the plasma processing space within the plasma processing chamber 102 to a desired vacuum condition. The gas exhaust unit 146 evacuates the inside of the plasma processing chamber 102 to thereby depressurize an inner pressure thereof up to a desired degree of vacuum.

An upper electrode 150 (that is, an upper electrode assembly), is an example of a first electrode and is positioned vertically above the lower electrode 116 to face the lower electrode 116 in parallel. The plasma generation space or process space PS 106 is defined between the lower electrode 116 and the upper electrode 150. The upper electrode 150 includes an inner upper electrode 152 having a disk shape, and an outer upper electrode 154 can be annular and surrounding a periphery of the inner upper electrode 152. The inner upper electrode 152 also functions as a processing gas inlet for injecting a specific amount of processing gas into the process space PS 106 above substrate W 110 mounted on the lower electrode 116.

More specifically, the inner upper electrode 152 includes electrode plate 156 (which is typically circular) having gas injection openings 158. Inner upper electrode 152 also includes an electrode support 160 detachably supporting an upper side of the electrode plate 156. The electrode support 160 can be formed in the shape of a disk having substantially a same diameter as the electrode plate 156 (when electrode plate 156 is embodied as circular in shape). In alternative embodiments, electrode plate 156 can be square, rectangular, polygonal, etc. The electrode plate 156 can be formed of a conductor or semiconductor material, such as Si, SiC, doped Si, Aluminum, and so forth. The electrode plate 156 can be integral with upper electrode 150 or detachably supported by electrode support 160 for convenience in replacing a given plate after surface erosion. The upper electrode 150 can also include a cooling plate or cooling mechanism (not shown) to control temperature of the electrode plate 156.

The electrode support 160 can be formed of, e.g., aluminum, and can include a buffer chamber 162. Buffer chamber 162 is used for diffusing process gas and can define a disk-shaped space. Processing gas from a process gas supply system 164 supplies gas to the upper electrode 150. The process gas supply system 164 can be configured to supply a processing gas for performing specific processes, such as film-forming, etching, and the like, on the substrate W 110. The process gas supply system 164 is connected with a gas supply line 166 forming a processing gas supply path. The gas supply line 166 is connected to the buffer chamber 162 of the inner upper electrode 152. The processing gas can then move from the buffer chamber 162 to the gas injection openings 158 at a lower surface thereof. A flow rate of processing gas introduced into the buffer chamber 162 can be adjusted by, e.g., by using a mass flow controller. Further, the processing gas introduced is uniformly discharged from the gas injection openings 158 of the electrode plate 156 (showerhead electrode) to the process space PS 106. The inner upper electrode 152 then functions in part to provide a showerhead electrode assembly.

A dielectric 168, having a ring shape, can be interposed between the inner upper electrode 152 and the outer upper electrode 154. An insulator 170, which can be a shield member having a ring shape and being formed of, e.g., alumina, is interposed between the outer upper electrode 154 and an inner peripheral wall of the plasma processing chamber 102 in an air tight manner.

The outer upper electrode 154 is electrically connected with a high-frequency power source 172 (first high-frequency power source) via a power feeder 174, an upper power feed rod 176, and a matching unit 178. The high-frequency power source 172 can output a high-frequency voltage having a frequency of 13 MHz (megahertz) or higher (e.g. 60 MHz), or can output a very high frequency (VHF) voltage having a frequency of 30-300 MHz. This power source 172 can be referred to as the main power supply as compared to a bias power supply. The power feeder 174 can be formed into, e.g., a substantially cylindrical shape having an open lower surface. The power feeder 174 can be connected to the outer upper electrode 154 at the lower end portion thereof. The power feeder 174 is electrically connected with the lower end portion of the upper power feed rod 176 at the center portion of an upper surface thereof. The upper power feed rod 176 is connected to the output side of the matching unit 178 at the upper end portion thereof. The matching unit 178 is connected to the high-frequency power source 172 and can match load impedance with the internal impedance of the high-frequency power source 172. Note, however, that outer upper electrode 154 is optional and embodiments can function with a single upper electrode.

Power feeder 174 can be cylindrical having a sidewall whose diameter is substantially the same as that of the plasma processing chamber 102. The ground conductor 180 is connected to the upper portion of a sidewall of the plasma processing chamber 102 at the lower end portion thereof. The upper power feed rod 176 passes through a center portion of the upper surface of the ground conductor 180. An insulating member 182 is interposed at the contact portion between the ground conductor 180 and the upper power feed rod 176.

The electrode support 160 is electrically connected with a lower power feed rod 184 on the upper surface thereof. The lower power feed rod 184 is connected to the upper power feed rod 176 via a connector. The upper power feed rod 176 and the lower power feed rod 184 form a power feed rod for supplying high-frequency electric power from the high-frequency power source 172 to the upper electrode 150. A variable condenser 186 is provided in the lower power feed rod 184. By adjusting the capacitance of the variable condenser 186, when the high-frequency electric power is applied from the high-frequency power source 160, the relative ratio of an electric field strength formed directly under the outer upper electrode 154 to an electric field strength formed directly under the inner upper electrode 172 can be adjusted. The inner upper electrode 152 of the upper electrode 150 is electrically connected with a low pass filter (LPF) 188. The LPF 188 blocks high frequencies from the high-frequency power source 172 while passing low frequencies from the high-frequency power source 130 to ground. A lower portion of the system, the susceptor 108, forming part of the lower electrode 120, is electrically connected with a high pass filter (HPF) 190. The HPF 190 passes high frequencies from the high-frequency power source 172 to ground.

High-frequency electric power in a range from about 3 MHz to 150 MHz, is applied from the high-frequency power source 172 to the upper electrode 150. This results in a high-frequency electric field being generated between the upper electrode 150 and the susceptor 108 or lower electrode 116. Processing gas delivered to process space PS 106 can then be dissociated and converted into a plasma. A low frequency electric power in a range from about 0.2 MHz to 20 MHz can be applied from the high-frequency power source 130 to the susceptor 108 forming the lower electrode 116. In other words, a dual frequency system can be used. As a result, ions in the plasma are attracted toward the susceptor 108, and thus anisotropy of etching is increased by ion assistance. Note that for convenience, FIG. 1 shows the high-frequency power source 172 supplying power to the upper electrode 150. In alternative embodiments, the high-frequency power source 172 can be supplied to the lower electrode 116. Thus, both main power (energizing power) and the bias power (ion acceleration power) can be supplied to the lower electrode.

Components of the plasma processing system 100 can be connected to, and controlled by, a control unit 192, which in turn can be connected to a corresponding storage unit 194 and user interface 196. Various plasma processing operations can be executed via the user interface 196, and various plasma processing recipes and operations can be stored in storage unit 194. Accordingly, a given substrate can be processed within the plasma processing chamber with various microfabrication techniques. In operation, the plasma processing apparatus uses the upper and lower electrodes to generate a plasma in the processing space PS 106. This generated plasma can then be used for processing a target substrate (such as substrate W 110 or any material to be processed) in various types of treatments such as plasma etching, chemical vapor deposition, treatment of glass material and treatment of large panels such as thin-film solar cells, other photovoltaic cells, and organic/inorganic plates for flat panel displays, etc.

The control unit 192 may include one or more processors, microcomputers, computing units and the like. The storage unit 194 may include memory, and is an example of non-transitory computer-readable storage media for storing instructions which are executed by the control unit 192, to perform the various functions described herein. For example, the storage unit 194 may generally include both volatile memory and non-volatile memory (e.g., RAM, ROM, or the like). Memory may be referred to as memory or computer-readable storage media herein. Memory is capable of storing computer-readable, processor-executable program instructions as computer program code that may be executed by the control unit 190 as a particular machine configured for carrying out the operations and functions described in the implementations herein.

Memory may further store one or more applications (not shown). The applications may include preconfigured/installed and downloadable applications. In addition, memory may store the spectrally—resolved light emission signals or spectral data used that are analyzed to generate the chemical—imprint identification of chemical species as described herein.

The plasma processing system 100 can further include a spectrometer 198 and a window 199. The spectrometer 198 is used for gathering spectral data that includes spectrally—resolved light emission signals from the plasma chamber. That is, different chemical specie or species may be gathered as spectrally—resolved light emission signals from the plasma chamber and at least one of these chemical species may be the source of anomalous events as described herein. The spectrometer 198 may be connected to control unit 192, or other controllers/systems.

The plasma processing system 100 can further include a photodiode (not shown) or any photo detector (not shown) that may be separately installed in addition to the spectrometer 198. For example, the photodiode may be used to detect the occurrence of the arcing event and as a consequence, this detection triggers spectral data analysis to determine chemical—imprint identifications of chemical specie(s) that may be the source of the arcing event. The photodiode may be connected to control unit 192, or other controllers/systems.

Figure 2:
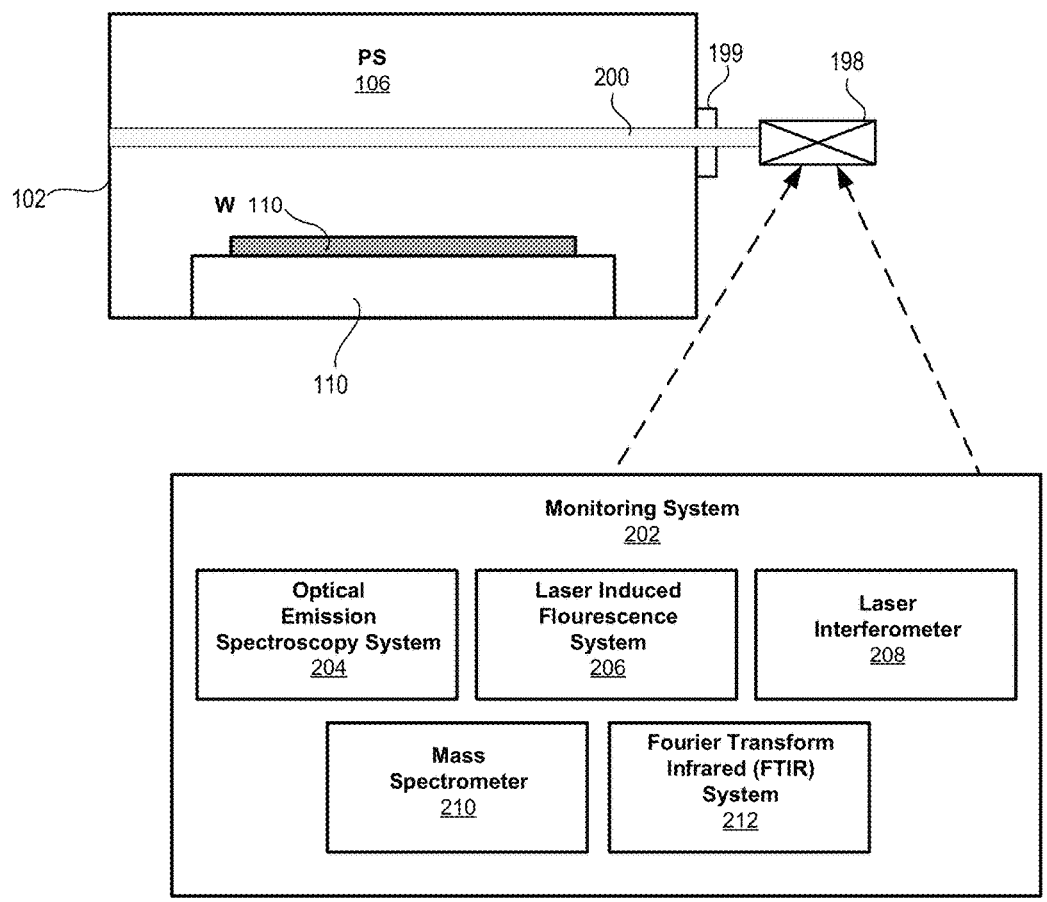
FIG. 2 is an example schematic block diagram of an example plasma processing system that implements spectra and plasma monitoring as described in accordance with embodiments herein.

FIG. 2 is an example schematic block diagram of an example plasma processing system that implements spectra and plasma monitoring. In an embodiment, the example plasma processing system may be used initially to manually define spectral characteristics of different chemical species utilized for each process step during the wafer fabrication process as further discussed below. Thereafter, the example plasma processing system may be used to gather spectral data during the actual wafer fabrication process and facilitate occurrence detection of the arcing events. The after-the-fact analysis of the gathered spectral data may be based upon observed time of occurrence of the arcing events and/or focused upon chemical specie(s) utilized in the process step corresponding to the observed time of occurrence.

As shown, a monitoring system 202 may be part of the spectrometer 198, which is a component of the plasma processing system 100. The monitoring system 202 may be used during the initial pre-identification of the spectral characteristics of each chemical specie for each process step in the wafer fabrication process. Thereafter, the monitoring system 202 may be used to gather spectra during a data acquisition cycle to generate the spectral data used for after-the-fact analysis of the anomalous event as described herein.

Components of the monitoring system 202 may include, but not limited to, an optical emission spectroscopy system 204, laser induced fluorescence system 206, laser interferometer 208, mass spectrometer 210, and Fourier transform infrared (FTIR) system 212.

In an embodiment, the optical emission spectroscopy system 204 may be used to obtain a spectrum or spectral data by analyzing light emission signals from a light volume 200. For example, with regard to the initial pre-identification of the spectral characteristics of each chemical specie for each process step in the wafer fabrication process, the optical emission spectroscopy system 204 may use the light volume 200 to establish distinct spectral characteristics of chemical specie(s) involved in the process step. In this example, the optical emission spectroscopy system 204 may utilize the other components such as the laser induced fluorescence system 206, etc.

For example, the optical emission spectroscopy system 204 utilizes the laser induced fluorescence system 206 that facilitates collection of spectra over a range of wavelengths when processing the light volume 200. Furthermore, the optical emission spectroscopy system 204 utilizes the laser interferometer 208 for a measurement method that uses a phenomenon of interference of waves. Furthermore still, the optical emission spectroscopy system 204 utilizes the mass spectrometer 210 to measure masses within a sample of the spectra during the data acquisition cycle. Furthermore still, the optical emission spectroscopy system 204 utilizes the FTIR system 212 in order to obtain infrared spectrum of absorption or emission of gas of the light volume 200 during the wafer fabrication process.

In an embodiment, and after the manual pre-identification of the spectral characteristics of each chemical specie for each process step in the wafer fabrication process, the chemical—imprint identifications may be stored in the storage unit 194 for future reference with regard to plasma monitoring.

During the plasma monitoring, the emission spectroscopy system 204 may be used to obtain the spectral data by similarly analyzing light emission signals from the light volume 200 during the actual wafer fabrication process. The obtained spectral data may include the spectrally-resolved light emission signals that may include chemical species that were pre-identified and whose spectral characteristics were stored at the storage unit 194. Upon detection of the occurrence of the anomalous event, an after-the-fact analysis of the obtained spectral data is implemented to determine which chemical specie(s) may have caused the anomalous event.

FIG. 3 is an example illustration of pre-identified chemical—imprint identifications chart 300 for different chemical species used in the wafer fabrication process as described herein. The spectrometer 198 and particularly, the emission spectroscopy system 204 above may facilitate manual or machine based pre-identification of chemical specie(s) 302 for each process step on the wafer fabrication process. For example, a light intensity for a chemical specie (e.g., chemical specie 302-2) may be analyzed on a particular wavelength (e.g., wavelength 304-2). In this example, the light intensity of the chemical specie 302-2 over the particular wavelength 302-2 may facilitate establishment of its distinct spectral characteristics as opposed to other chemical species 302-4, 302-6, etc. In another example, the spectrometer 198 may be locked on the light intensity of the chemical specie 302-2 and the locked light intensity is analyzed on a range of wavelengths to establish its distinct spectral characteristics.

During the plasma monitoring, and for each process step, all of the chemical species 302 may not be visible at all through the spectrometer 198. For example, for the process step of oxidation of silicon, a Silicon (Si) 302-40 reacts with an oxygen gas ($O_2$) at an elevated temperature during dry oxidation. The oxygen gas may be fed through the inner upper electrode 152 that also functions as the processing gas inlet for injecting a specific amount of processing gas into the process space PS 106. In this example, the spectrometer 198 may detect the chemical species Si and $O_2$ while light intensities from other chemical species 302 may not be visible or barely visible.

Referencing the chart 300, the different wavelengths 304 may correspond to the light intensities of different chemical species 302. In the example process step above (i.e., oxidation of silicon), the spectrometer 198 may be dialed to scan wavelengths 213.9 nm (i.e., wavelength 304-2) to 798.6 nmn (i.e., wavelength 304-n) and the spectral data may generate light intensities for the chemical species Si and $O_2$ while the light intensities corresponding to the rest of the chemical species 302 may not be visible or barely visible.

Figure 4:
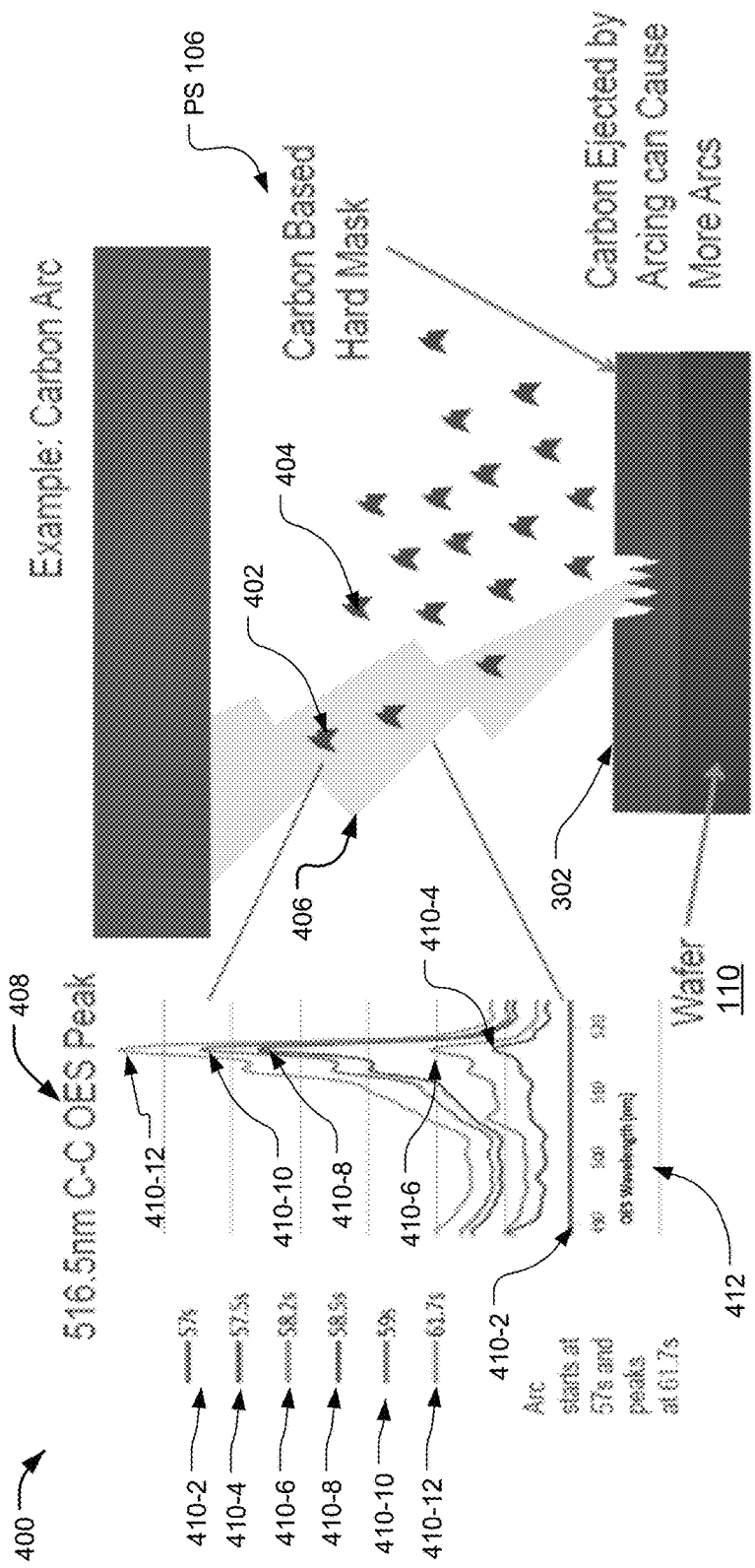
FIG. 4 is an example illustration of after-the-fact evaluation of an anomalous event composition from spectral data as described herein.

FIG. 4 is an example illustration of after-the-fact evaluation of an anomalous event composition 400 from the spectral data as described herein. As shown, the anomalous event composition 400 includes particles 402 and 404, an arcing event 406, a spectral data 408, particular time instant 410 representing time of occurrence of the arcing event 406, the wavelengths 412 of the spectral data 408, PS 106, wafer 110, and chemical specie 302.

The arcing event 406, which may be a sudden spike of voltage and/or current resulting to a high transient signal, may generally occur and observed from the PS 106, which may be defined by the space in between electrodes (i.e., anode and cathode electrodes). For example, when the particles 402 from the chemical specie 302 produce an electric field that is greater than a plasma breakdown voltage, the arcing event 406 may be generated all the way from the cathode electrode to the anode electrode. As a result, additional particles 404 may be generated and the particles 404 may further enhance or exaggerate the sudden spike of voltage and/or current resulting to the transient signal—arcing event 406.

The spectral data 408 may include the spectra during a particular instant (i.e., particular time instant 410) of occurrence of the arcing event 406. That is, the spectral data 408 may include a targeted portion of the spectrum or total spectral data gathered by the spectrometer 198 from the PS 106. As discussed above, the particular instant 410 may be based through manual and visual observation of actual occurrence of the arcing events 406. For the example anomalous event composition 400, the manually observed visual occurrence of the arcing event 406 may be represented by the particular time instants 410-2 to 410-12.

In another scenario, the photodiode may be utilized to detect the time of occurrence of the arcing event 406. For example, the detection by the photodiode may utilize the threshold value and the detection may trigger a point of reference as to how the spectral data is analyzed i.e., after-the-fact. In the example anomalous event composition 400 above, the point of reference may be represented by the particular time instants 410-2 to 410-12. In this case, the analysis of the spectral data may focus on the spectra acquired during these particular time instants 410-2 to 410-12.

As shown, the arcing event 406 starts at around 57 s (i.e., particular time instant 410-2) and peaks at around 61.7 seconds (i.e., particular time instant 410-12) of the spectral data 408.

Referencing back FIG. 3, the spectrometer 198 gathers the spectral data 408 by scanning the wavelengths 304-2 (i.e., 213.9 nm) to 304-n (i.e., 789.6 nm). For the particular time instants 410-2 to 410-12, few chemical species 302 may be observed for the wavelengths 412 (i.e., 490 nm to 520 nm) of the spectral data 408. Thus, the light intensities for the wavelengths 412 (i.e., 490 nm to 520 nm) are identified with regard to their distinct chemical—imprint identifications.

For example, as shown in the Chart 300, the wavelengths 412 (i.e., 490 nm to 520 nm) may possibly include chemical species H (for Hydrogen), He (for Helium), O (for Oxygen), C2 (for two carbon alkene) and CO (for Carbon Oxide). In relation to the spectral data 408, the chemical specie for the particular instant time 410-12 may either be H, He, O, C2 and/or CO. The rest of the chemical species may not be visible with the wavelengths 412.

In an embodiment, the arcing event 406 (i.e., anomalous event) may be classified based on the spectral signature of the at least one or more chemical species. Furthermore, a source or surface of the arcing event is determined and identified, respectively, as to where it evolved in the plasma processing chamber. In other words, whether the arcing event 406 has affected surfaces of aluminum support of electrodes, alumina inner wall of the plasma processing chamber, the wafer 110, the conductor or semiconductor material of the electrode plate 156, and the like. With this, identifying a location from which the at least one chemical species associated with the identified spectral signature have evolved into the plasma processing chamber may be implemented as well.

In another embodiment, plasma electrical characteristics (i.e., electrical characteristics of the arcing event 406) may be measured and this measurement may be associated with behavior of the plasma electrical parameter during the anomalous event. The plasma electrical parameter may include the parameter of RF power, substrate holder RF power, and a plasma potential.

In another embodiment, a dedicated arc detector controller such as the photodiode may be utilized to process the spectrally-resolved light emission signal of the gathered spectrum from the PS 106. In this embodiment, the arc detector controller may be configured to detect the arcing event 406 using both the acquired spectrally-resolved light emission signal and acquired non-spectrally resolved light emission signal (i.e., chemical species that may not have been identified through their distinct spectral characteristics). The processing of the spectrally-resolved light emission signal may be performed in a plasma endpoint detector controller.

Figure 5:
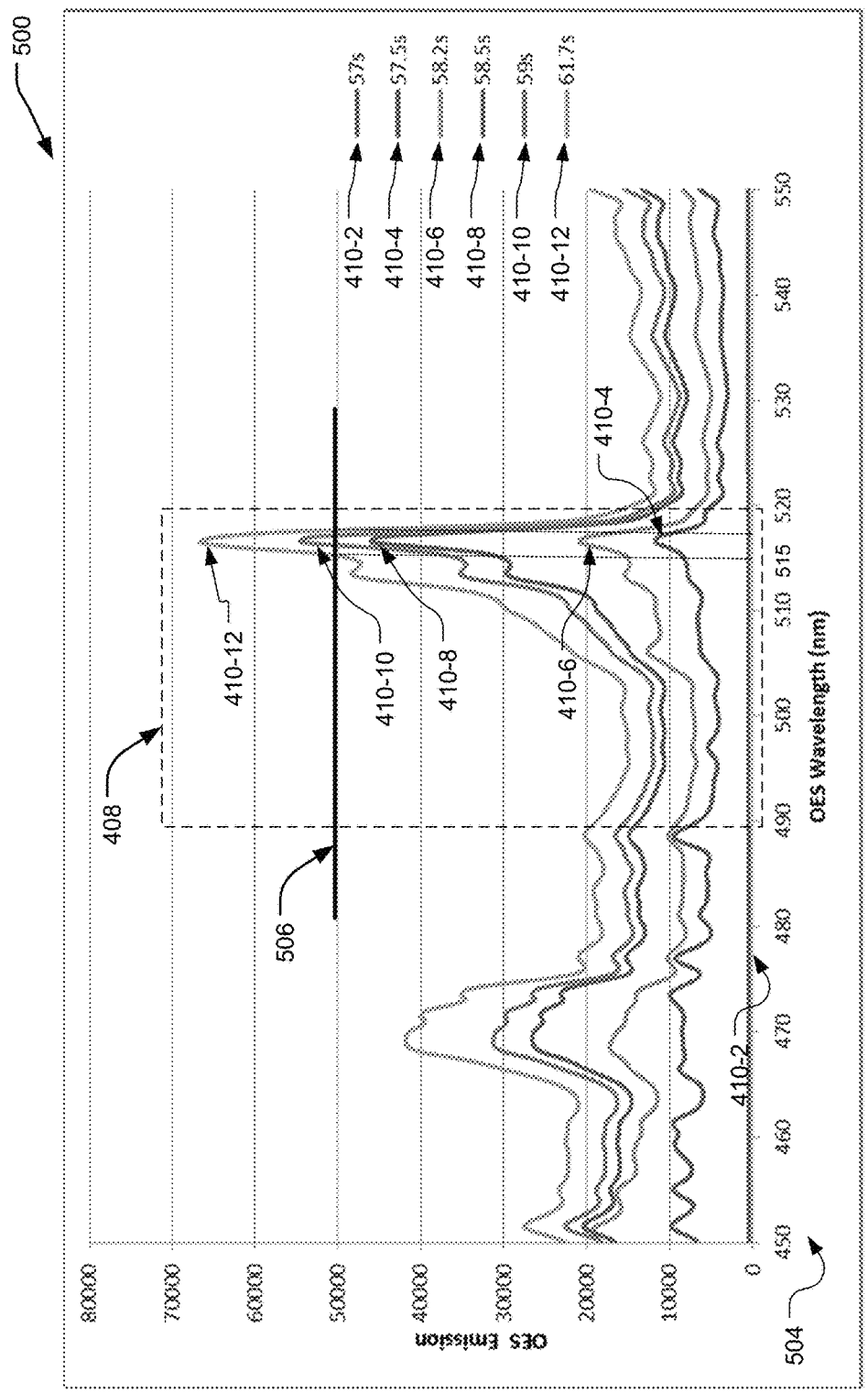
FIG. 5 is an example spectral data that may be utilized to analyze sources of anomalous events as described herein.

FIG. 5 is an example spectral data 500 that may be utilized to analyze the source of the anomalous events as described herein.

After the detection of the occurrence of the anomalous event through visual observation or through the use of the photodiode detector, the portions of the spectral data such as the spectral data 500 may be analyzed to determine the chemical specie(s) that may have generated the anomalous events.

As shown, the spectral data 500 includes wavelengths 502 that defines measurements along horizontal x-axis, light emission signal intensities 504 that defines measurements for vertical y-axis, a threshold 506, and the particular time instants 410-2 to 410-12. Furthermore, the spectral data 500 shows the spectral data 408 similar to the spectral data generated by the arcing event 406 of FIG. 4. Furthermore still, the spectral data 500 shows a threshold 506 that may be used to determine the chemical specie(s) that may be present or may be the sources of the anomalous event.

In an embodiment, the threshold 506 may include a pre-configured value that may be used to determine presence of the arcing event 406. As shown, the particular time instants 410-10 (i.e., 59 seconds and 410-12 (i.e., 61.7 seconds) may be the focus of spectral data analysis with regard to sources of the arcing event 406. The reason being, the particular time instants 410-10 and 410-12 are above the threshold 506.

The wavelengths 504 that correspond to the particular time instants 410-10 and 410-12 (i.e., which are above the threshold 506) may be determined to include the wavelengths 515-518 nm as shown.

Referencing back FIG. 3, the wavelengths 515-518 nm may correspond to include the chemical species Helium (He) and Carbon Oxide. Accordingly, the anomalous events may be determined to have generated by at least the chemical species He and CO.

Figure 6:
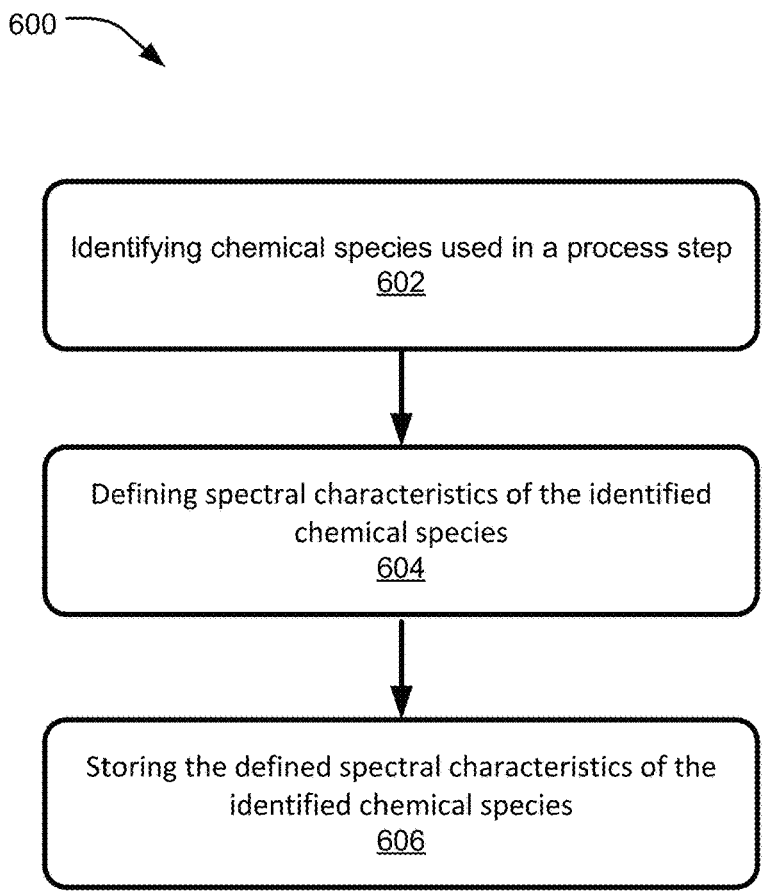
FIG. 6 shows an example process for establishing chemical—imprint identifications for identifying different chemical specie during a wafer fabrication process in a plasma processing system.

FIG. 6 shows an example process 600 for establishing chemical—imprint identifications for identifying different chemical specie during a wafer fabrication process in a plasma processing system. The pre-identification of the different chemical specie may be performed manually for each chemical specie that may be used on a particular process step during the wafer fabrication process. The order in which the method is described is not intended to be construed as a limitation, and any number of the described method blocks can be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 602, identifying chemical species that are used in a process step for a wafer fabrication process is performed. There are multiple process steps performed on a wafer from an initial oxidation to electrical testing. For example, the initial oxidation may utilize molecular oxygen as oxidant during thermal oxidation. In this example, the molecular oxygen may be identified to be one of the chemical species used in this initial oxidation process step.

At block 604, defining spectral characteristics of the identified chemical species is performed. For example, for the molecular oxygen chemical specie, the spectrometer 198 may be used to detect and acquire distinct light intensity characteristics of the molecular oxygen over a particular wavelength or over a range of wavelengths. In this example, the distinct light intensity characteristics of the molecular oxygen over the particular wavelength or range of wavelengths may define its chemical—imprint signature.

Referencing the pre-identified chemical—imprint identifications chart 300 for different chemical species as discussed above in FIG. 4, each wavelength 304 setting of the spectrometer 198 may be configured to receive corresponding light intensity signal for each chemical specie 302. That is, the spectrometer 198 may be configured to measure each chemical specie for each wavelength from wavelengths 213.9 nm (i.e., wavelength 304-2) to 789.6 nm (i.e., wavelength 304-n).

At block 606, storing the defined spectral characteristics of the identified chemical species is performed. For example, the chemical—imprint signatures (i.e., defined spectral characteristics) of each identified chemical specie may be store in the storage unit 194. In this example, the stored chemical-imprint signatures may be used as reference for identifying the spectrally-resolved light emission signals during the after-the-fact analysis of the spectral data.

Figure 7:
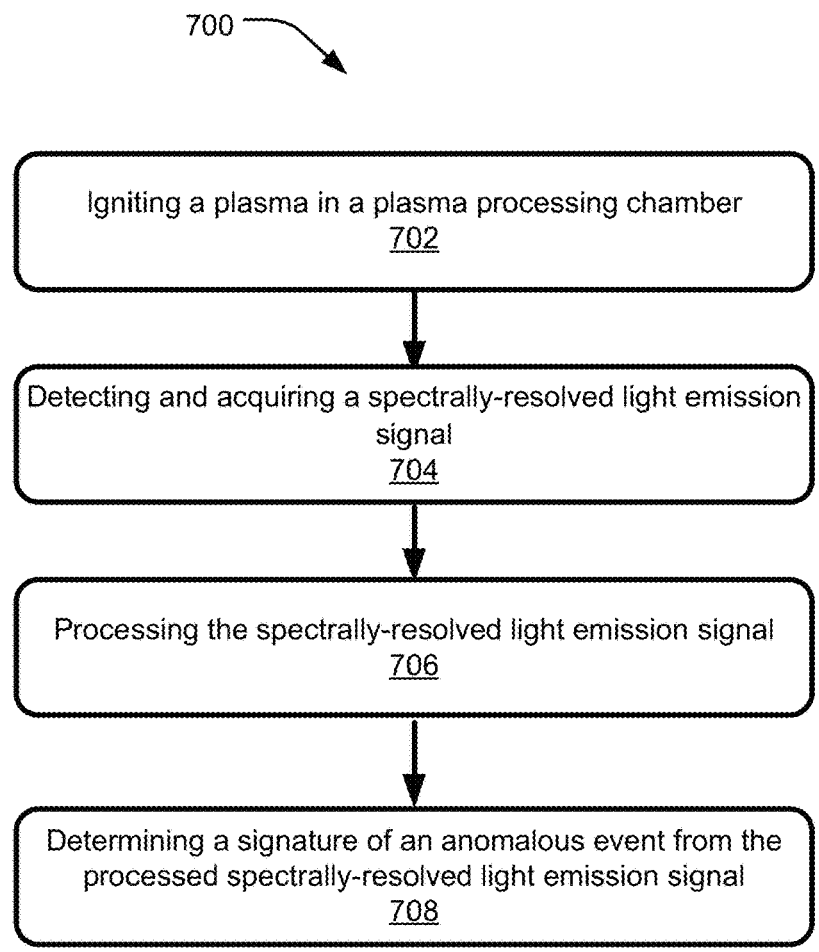
FIG. 7 shows an example process for monitoring and detecting anomalous events during a wafer fabrication process in a plasma processing system.

FIG. 7 shows an example process 700 for monitoring and detecting anomalous events during a wafer fabrication process in a plasma processing system. In an embodiment, the analysis of the spectral data is implemented after the occurrence of the arcing event. The order in which the method is described is not intended to be construed as a limitation, and any number of the described method blocks can be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 702, igniting a plasma in a plasma processing chamber during a wafer fabrication process is performed. For example, the igniting may involve artificial production of plasmas during reactive-ion etching, sputtering, plasma-enhanced chemical vapor deposition, and the like, in the wafer fabrication process. Referencing FIG. 1 above, the ignited plasma may be introduced in the plasma generation space PS 106, which is in between the lower electrode 116 and the upper electrode 150. The inner upper electrode 152 may function as the processing gas inlet for injecting the specific amount of processing gas (as required by the current process step) into the PS 106, which is above the substrate W 110 and mounted on the lower electrode 116.

At block 704, detecting and acquiring a spectrally-resolved light emission signal is performed. For example, the spectrometer 198 collects the light volume 200 as shown in FIG. 2 above. The light volume 200 may be taken from the PS 106, which is above the substrate W 110. In this example, the light volume 200 may include the spectrally-resolved light emission signals and other light emissions or spectra from the plasma processing chamber as well. The other light emissions or spectra may be treated as non-spectrally-resolved light emission signals to be identified through the spectrometer 198.

At block 706, processing the spectrally-resolved light emission signal is performed. For example, the spectrometer 198 may forward the gathered spectral data to the control unit 192, which may include one or more processors, microcomputers, computing units and the like, for the processing of the spectral data. The processing, in this example, may involve identification of the light intensity signals that are above the threshold 506. For the light intensity signals that are above the threshold 506, the corresponding wavelength 304 may be utilized by the control unit 192 to identify the chemical species using the chemical-imprint signatures stored at the storage unit 194.

At block 708, determining a signature of an anomalous event from the processed spectrally-resolved light emission signal is performed. For example, and after the occurrence of the anomalous event (i.e., arcing event), the spectral data is analyzed to determine the chemical—imprint signature(s) of the chemical specie(s) that may have generated the arcing events or plasma instability. In this example, a manual reference point for the analysis of the spectral data may be implemented.

For example, the anomalous event was visually observed to have occurred at a particular time instants 410-2 to 410-12 (i.e., reference point) of the data acquisition cycle. In this example, the analysis of the spectral data and particularly, the determining of the chemical imprint—identifications may be based from the spectra acquired within the particular time instants 410-2 to 410-12. Typically, the chemical specie(s) with light intensities that are above threshold 506 may be considered to be sources of the anomalous events.

In another embodiment, the photodiode may detect the occurrence of the anomalous events and this detection may trigger analysis of the spectral data similar to the implementation of the manual reference above. That is, the reference point is based from the time that the photodiode detected the occurrence of the anomalous event. The spectral data acquired within a few micro seconds before and/or after the reference point may then be analyzed to determine the chemical—imprint signature of the chemical species that caused the arcing events.

With the analyzed anomalous event, a recording of the anomalous event for fault detection and/or notification plasma processing system Operator may be implemented. Furthermore, setting the controller unit to prevent operation of the plasma processing system at conditions identified to be associated with the anomalous event may further be implemented.

What is claimed is:

1. A method for detection of anomalous events in a plasma processing system, comprising:
    igniting a plasma in a plasma processing chamber;
    detecting a non-spectrally resolved light emission signal and a spectrally-resolved light emission signal from the plasma in the plasma processing chamber, the non-spectrally resolved light emission signal and the spectrally-resolved light emission signal including light emissions from an anomalous event;
    detecting a time of the anomalous event from the non-spectrally resolved light emission signal;
    selecting a portion of the spectrally-resolved light emission signal in accordance with the time of the anomalous event detected from the non-spectrally resolved light emission signal;
    processing the selected portion of the spectrally-resolved light emission signal; and
    detecting a signature of the anomalous event from the processed spectrally-resolved light emission signal.

2. The method of claim 1, wherein the anomalous event comprises an arcing event or a plasma instability.

3. The method of claim 1, further comprising:
    recording the anomalous event for fault detection or notifying the plasma processing system operator, or both.

4. The method of claim 1, further comprising,
    identifying the spectral signature of at least one chemical species from the processed spectrally-resolved light emission signal.

5. The method of claim 4, further comprising:
    classifying the anomalous event based on the identified spectral signature of the at least one chemical species.

6. The method of claim 4, further comprising:
    determining a source from where the at least one chemical species associated with the identified spectral signature have evolved, into the plasma processing chamber, during the anomalous event.

7. The method of claim 4, further comprising:
    identifying a surface from which the at least one chemical species associated with the identified spectral signature have evolved, into the plasma processing chamber, during the anomalous event.

8. The method of claim 4, further comprising:
    identifying a location from which the at least one chemical species associated with the identified spectral signature have evolved, into the plasma processing chamber, during the anomalous event.

9. The method of claim 1, further comprising: measuring a plasma electrical parameter; associating the behavior of the plasma electrical parameter during the anomalous event, with the anomalous event.

10. The method of claim 9, wherein the plasma electrical parameter comprises a parameter selected from the group including radio frequency (RF) power, substrate holder RF power, and plasma potential.

11. The method of claim 9, further comprising:
    setting the controller to prevent operation of the plasma processing system at conditions identified to be associated with the anomalous event.

12. The method of claim 1, wherein the spectrally-resolved light emission signal is detected using a spectrometer.

13. The method of claim 1, wherein the processing the spectrally-resolved light emission signal is performed in a dedicated arc detector controller.

14. The method of claim 13, wherein the arc detector controller is configured to receive the non-spectrally resolved light emission signal from a high-speed non-spectrally resolved arc detector.

15. The method of claim 14, wherein the arc detector controller is configured to detect an arcing event using both the detected spectrally-resolved light emission signal and the detected non-spectrally resolved light emission signal.

16. The method of claim 1, wherein the processing the spectrally-resolved light emission signal is performed in a plasma endpoint detector controller.

17. An apparatus for detection of anomalous events in a plasma processing system, comprising:
    a window disposed on a plasma processing chamber of the plasma processing system, for providing optical access to the plasma processing chamber;
    a detector for detecting a non-spectrally resolved light emission signal inside the plasma processing chamber;
    a spectrometer for detecting a spectrally-resolved light emission signal inside the plasma processing chamber, through the window; and
    a controller configured to
        detect a time of the anomalous event from the non-spectrally resolved light emission signal;
        select a portion of the spectrally-resolved light emission signal in accordance with the time of the anomalous event detected from the non-spectrally resolved light emission signal; and
        process and determine chemical species that caused the anomalous event from the selected portion of the spectrally-resolved light emission signal.

18. The apparatus of claim 17 further comprising a store of spectrally-resolved light emission signals comprising previously pre-identified, stored, and used for reference in an after-the-fact analysis of spectral data to identify the chemical species that caused anomalous events.

19. The apparatus of claim 18, wherein the detector comprises a photodiode detector configured to detect occurrence of arcing events and particular time instant of the occurrence of the arcing events.

20. The apparatus of claim 17, wherein the determination of the chemical species is based upon their corresponding chemical—imprint identifications.

* * * * *